United States Patent
Maier

(10) Patent No.: US 6,756,216 B2
(45) Date of Patent: Jun. 29, 2004

(54) PROCESS FOR PRODUCING NON-PROTEINOGENIC L-AMINO ACIDS BY FERMENTATION

(75) Inventor: Thomas Maier, Dachau (DE)

(73) Assignee: Consortium für Elektrochemische Industrie GmbH, München (DE)

( * ) Notice: Subject to any disclaimer, the term of this patent is extended or adjusted under 35 U.S.C. 154(b) by 0 days.

(21) Appl. No.: 09/957,961

(22) Filed: Sep. 21, 2001

(65) Prior Publication Data

US 2002/0039767 A1 Apr. 4, 2002

(30) Foreign Application Priority Data

Sep. 21, 2000 (DE) .......................................... 100 46 934

(51) Int. Cl.$^7$ .......................... C12P 13/04; C12P 13/12; C12N 1/00
(52) U.S. Cl. ........................ 435/106; 435/113; 435/849
(58) Field of Search ................................ 435/106, 113, 435/849

(56) References Cited

U.S. PATENT DOCUMENTS

| | | | |
|---|---|---|---|
| 4,879,223 A | * | 11/1989 | Miyazawa et al. |
| 5,646,167 A | | 7/1997 | MacPherson et al. |
| 5,972,663 A | | 10/1999 | Winterhalter et al. |
| 6,191,168 B1 | * | 2/2001 | Rubenstein |

FOREIGN PATENT DOCUMENTS

| | | |
|---|---|---|
| DE | 19949579 | 11/2000 |
| EP | 29998 | 3/1985 |
| EP | 885 962 | 12/1998 |
| WO | 9715673 | 5/1997 |
| WO | 9814602 | 4/1998 |

OTHER PUBLICATIONS

Saito et al; Biological and Pharmaceutical Bulletin, Tokyo, JP, vol. 20, No. 1, Jan. 1997, pp. 47–53.
Nakamoni et al; Applied and Environmental Microbiology, Washington, DC, US, vol. 64, No. 5, May 1998 pp. 1607–1611.
Denk et al; Journal of Microbiology, Society for Microbiology, reading, GB, vol. 133, No. 3, Mar. 1, 1987, pp. 515–525.
Topczewski et al; Current Genetics, New York, NY, US, vol. 31, No. 4; Apr. 1997, pp. 348–356.
Chemical Abstract, DN 123: 163090, for Gaskin, Peter J. et al..
Chemical Abstract, DN 120:99262, for Tai, Abraham et al..
Chemical Abstract, DN 88:165656, for Grzonka, Z. et al.
Chemical Abstract DN 77:70746 for Votruba, Ivan et al.
Chemical Abstract DN 109: 190731 for Pal, Bimal et al.
Chemical Abstract DN 101:71202 for Wislocki, Peter G. et al.
Chemical Abstract DN 120: 271118 for Girard, Michel et al.
Chemical Abstract DN 123: 163090 for Gaskin, Peter J. et al.
Chemical Abstract DN 135: 19890 for Sagiyan, A. S. et al.
Chemical Abstract vol. 126:143319 (1997) pp. 47–53 corresp. to Biol. Pharm. Bull.
Chemical Abstract vol. 51 1291g (1957) corresp. JP 30000619.
Rahm et al., Biotechnology 1996; vol. 6, pp. 505–560.
Saito et al., Biol. Pharm. Bull 1997, 20 : pp. 47–53.
Nakamori S. et al., Applied and Environmental Microbiology May 1998, vol. 64, No. 5, pp. 1607–1611.
Takagi H. et al., FEBS Letters 452 (1999) pp. 323–327.
English Derwent Abstract AN 1981–44417 D [25] corresp. to EP 29998 B1.
English Derwent Abstract AN 2000–648385 [63] corresp. to DE 19949579.
English Derwent Abstract AN 1997–246368 [23] corresp. to WO 97/15673.

* cited by examiner

*Primary Examiner*—Christopher R. Tate
(74) *Attorney, Agent, or Firm*—Collard & Roe, P.C.

(57) ABSTRACT

Process for production of non-protenogenic L-amino acids by direct fermentation of a microorganism strain known per se having a deregulated cysteine metabolism in a manner known per se, which comprises adding, during the fermentation, a nucleophilic compound to the fermentation batch in a manner such that this leads to the production of non-proteinogenic L-amino acids by the microorganism strain.

3 Claims, No Drawings

PROCESS FOR PRODUCING NON-PROTEINOGENIC L-AMINO ACIDS BY FERMENTATION

BACKGROUND OF THE INVENTION

1. Field of the Invention

The present invention relates to a process for producing non-proteinogenic L-amino acids by direct fermentation of microorganisms, and to L-amino acids obtained by the process.

2. The Prior Art

Non-proteinogenic amino acids are amino acids which are not used in nature as building blocks for protein biosynthesis and as a result may be clearly differentiated from the 20 proteinogenic amino acids. They are preferably β-substituted L-alanine derivatives.

Non-proteinogenic amino acids are compounds of interest, for example, for the preparation of pharmaceuticals and agricultural active compounds. They can, as active compound or as a part of an active compound imitate, in a type of molecular mimicry, the structure of natural amino acids and as a result, for example, in receptor interactions cause a modulation of the natural reaction. In addition, they can serve quite generally as synthesis building blocks as chiral compounds in the context of the "chiral pool".

Previous production processes for non-proteinogenic amino acids in enantiomerically pure form are generally based on complex syntheses which generally only permit access to a defined compound. Only a few processes enable different compounds to be produced by simple replacement of a starting material.

In most cases chemical syntheses are involved which themselves mostly start from the beginning from chiral building blocks or are followed by a racemate resolution.

Alternatively, some enzymatic processes are described. Thus, using transaminases, various non-proteinogenic amino acids can be prepared from α-keto acids using L-glutamic acid as amino donor. A different process utilizes hydantoinases in combination with carbamoylases. However, enzymatic processes are also cost-intensive, since the corresponding enzymes must be provided and these have only a limited life as catalysts (Rehm et al., Biotechnology 1996; Vol. 6, pp. 505–560).

In contrast, processes for producing non-proteinogenic amino acids by direct fermentation of microorganisms would be particularly simple and expedient. However, such processes have the risk that the non-proteinogenic amino acid produced interferes with the metabolism of the natural amino acids and thus growth inhibition occurs. Previously, within this subject area, a process for the direct fermentation of D-amino acids has been disclosed (WO98/14602). This application describes the production of D-amino acids by recombinant microorganisms into which a D-amino transferase gene and an L-amino deaminase gene have been introduced. Furthermore, Saito et al. (Biol. Pharm. Bull. 1997, 20: 47–53) described the production of the plant non-proteinogenic amino acid L-pyrazolylalanine by expressing plant genes in *Escherichia coli*. The yields, however, are too low for commercial production, at <1 g/l, and the costs, with the described use of L-serine as starting material, are very high.

SUMMARY OF THE INVENTION

It is an object of the present invention to provide an efficient process for producing a series of non-proteinogenic L-amino acids by direct fermentation.

This object is achieved according to the invention by a microorganism strain known per se having a deregulated cysteine metabolism being fermented in a manner known per se which comprises, during the fermentation, adding a nucleophilic compound to the fermentation batch in amounts such that this leads to the production of non-proteinogenic L-amino acids by the microorganism strain.

Preferably, at the end of the fermentation, the non-proteinogenic L-amino acids are separated off from the respective fermentation batch by means of methods known per se.

Surprisingly, it has been found that in the fermentation of microorganism strains having deregulated cysteine metabolism, instead of sulfide, a series of other nucleophilic compounds enter very efficiently into amino acid metabolism and the corresponding reaction products are excreted into the culture medium. Advantageously, glucose can be used here as an inexpensive source of carbon.

By means of the inventive addition of nucleophilic compounds during the fermentation, non-proteinogenic L-amino acids are accordingly formed. Preferably, therefore, a nucleophilic compound which enters into amino acid metabolism is added during the fermentation.

Preferably, nucleophilic compounds are added which comprise a radical selected from the group consisting of

Particularly preferably, a nucleophilic compound selected from the following group is added to the fermentation batch:

Thiol of the general formula (1):

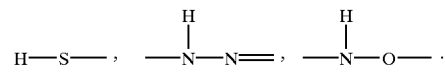

where $R^1$ is monovalent substituted or unsubstituted alkyl, alkoxy, aryl or heteroaryl radical having a maximum of 15 carbon atoms;

azole of the general formula (2) or (3):

and their esters, ethers or salts, where X and Y are identical or different and denote $CR^4$ or N, and $R^4$ is —H, —COOH, —OH, —NH$_2$, —NO$_2$, —SH, —SO$_3$, —F, —Cl, —Br, —I, $C_1$-$C_5$-alkylcarbonyl or $R^1$, and $R^1$ has the meaning specified under formula (1) and where $R^2$ and $R^3$ are identical or different and are $R^4$ or where $C^1$ and $C^2$ in formula (3), instead of the substituents $R^2$ and $R^3$, are linked by means of a bridge [—$CR^5R^6$—]$_a$, where a is 1, 2, 3 or 4, to form a ring, where $R^5$ and $R^6$ are identical or different and are $R^4$ and one or more non-adjacent groups [—$CR^5R^6$—] can be replaced by oxygen, sulfur, or an imino radical, which may be unsubstituted or substituted by $C_1$–$C_5$-alkyl, and two adjacent groups [—$CR^5R^6$—] can be replaced by a group [—$CR^5$=$CR^6$—] or by a group [—$CR^5$=N—].

Isoxazolinone of the general formula (4) or (5):

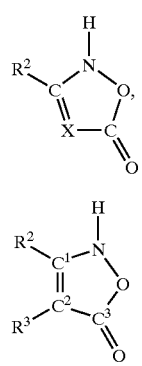

(4)

(5)

and their esters, ethers or salts,
where X, $R^1$, $R^2$, $R^3$ have the meaning specified above and where $C^1$ and $C^2$ in formula (5), instead of the substituents $R^2$ and $R^3$, can be linked by means of a bridge defined as for formula (3) to form a ring.

Examples of thiols are compounds selected from the group consisting of 2-mercaptoethanol, 3-mercaptopropanol, 3-mercaptopropionic acid, 3-mercapto-1-propanesulfonic acid, mercaptoethanesulfonic acid, 2-mercaptoethylamine, thioglycolic acid, thiolactic acid, thioacetic acid, mercaptosuccinic acid, mercaptopyruvic acid, dithiothreitol, dithioerythritol, 1-thioglycerol, thiophenol, 4-fluorothiophenol, 4-mercaptophenol, p-thiocresol, 5-thio-2-nitrobenzoic acid, 2-mercaptothiazole, 2-mercaptothiazoline, 2-mercaptoimidazole, 3-mercapto-1,2,4,-triazole, 2-thiophenethiol, 2-mercaptopyridine, 2-mercaptopyrimidine, 2-thiocytosine, 2-mercaptonicotinic acid, 2-mercapto-1-methylimidazole, 2-mercaptobenzothiazole, 2-mercaptobenzoxazole, 6-mercaptopurine.

Examples of azoles are compounds selected from the group consisting of 1,2-pyrazole, 3-methylpyrazole, 4-methylpyrazole, 3,5-dimethylpyrazole, 3-aminopyrazole, 4-aminopyrazole, pyrazole-4-carboxylic acid, pyrazole-3,5-dicarboxylic acid, 1,2,3-triazole, 1,2,4-triazole, 3-amino-1,2,4-triazole, 1,2,3,4-tetrazole, indazole, indazole-3-carboxylic acid, indazole-5-carboxylic acid, 5-aminoindazole, benzotriazole, benzotriazole-5-carboxylic acid, 5-aminobenzotriazole, aminopyrazolopyrimidine, 8-azaguanine, 8-azaadenine.

Examples of isoxazolinones are compounds selected from the group consisting of isoxazolin-2-one, 4-methylisoxazolin-2-one, 5-methylisoxazolin-2-one, 4,5-dimethylisoxazolin-2-one, 1,2,4-oxadiazolidin-3,5-dione.

Microorganism strains having deregulated cysteine metabolism that can be used in the inventive process are known from the prior art. They are distinguished by endogenous production of O-acetyl-L-serine, the immediate biosynthetic precursor of L-cysteine, which is increased in comparison with the wild type-strain. In a microorganism, it is known that in the last step of cysteine biosynthesis, due to the activity of O-acetyl-serine-sulfhydrylases, the acetyl function of the O-acetyl-L-serine is replaced by a thiol function and L-cysteine is thus formed. This reaction type is termed β-substitution, since at the β-carbon atom of the amino acid, a functional group is replaced.

Preferably, one of the following microorganism strains is used in the inventive process:
strains having modified cysE alleles, for example as described in WO 97/15673 (hereby incorporated by reference) or Nakamori S. et al., 1998, Appl. Env. Microbiol. 64: 1607–1611 (hereby incorporated by reference) or Takagi H. et al., 1999, FEBS Lett. 452: 323–327, or
strains which contain efflux genes, as described, for example, in EP 0885962 A1 (equivalent to the U.S. application having the Ser. No. 09/097759 (hereby incorporated by reference)), or
strains having a modified CysB activity, as described in German patent application DE 19949579, or
strains which have been produced using nonspecific mutagenesis methods combined with screening methods for cysteine overproduction or reduced cysteine degradation, as described, for example, in WO 97/15673, or in Nakamori S. et al., 1998, Appl. Env. Microbiol. 64: 1607–1611.

Such strains are distinguished by the fact that, under adequate supply of an inorganic sulfur source, for example sulfate or thiosulfate, they excrete significant amounts of L-cysteine or a derivative thereof into the culture medium. As a result of the inventive addition of a nucleophilic compound during the fermentation, this compound enters into the β-substitution and leads as a result to the production of non-proteinogenic L-amino acids.

With microorganism strains which do not have deregulated cysteine metabolism (for example the customary wild type organisms), such a procedure leads to slowing of cysteine biosynthesis and thus to growth inhibition. Therefore, no non-proteinogenic amino acids are formed in significant amounts.

Since the inventively used strains, however, have deregulated cysteine metabolism and thus a high endogenous level of O-acetyl-L-serine, it is possible to produce the non-proteinogenic L-amino acid in large amounts. At the same time, sufficient formation of L-cysteine is still ensured in order to guarantee cell growth of the microorganism.

Microorganism strains preferably used are those of the species *Escherichia coli* that have deregulated cysteine metabolism.

Preferably, these are *Escherichia coli* strains as described, for example, in WO 97/15673 or in EP 0885962 A1 (equivalent to the U.S. application having the Ser. No. 09/097759) or in DE 19949579. According to the processes described in these patent applications, cysteine metabolism can be deregulated in any strains by transformation with a plasmid that carries, for example, a feedback-resistant cysE allele and/or an efflux gene.

The inventive process for producing the non-proteinogenic L-amino acids using a microorganism strain is carried out in a fermenter in a manner known per se, but with additional addition of a nucleophilic compound.

The microorganism strain is grown in the fermenter as a continuous culture, as batch culture or, preferably, as fed-batch culture. Particularly preferably, a carbon source and a nucleophilic compound are continuously added during the fermentation.

Addition of the nucleophilic compound begins after inoculation, or, preferably, after an initial growth phase. Particularly preferably, the addition begins 6–8 hours after the start of fermentation and lasts until the end of fermentation.

The amount of added nucleophilic compound depends on its toxicity for the microorganism and is in the range from 10 to 1 000 mmol per liter of initial volume of the fermentation medium. Particular preference is given to an addition of 50 to 500 mmol per liter of initial volume of the fermentation medium.

Carbon sources for the fermentation are preferably sugars, sugar alcohols or organic acids. Particularly preferably in the inventive process, the carbon sources used are glucose, lactose or glycerol.

Preferably, glucose is added in a form which ensures that the content in the fermenter is kept in a range of 0.1–50 g/l during the fermentation. Particular preference is given to a range of 0.5–10 g/l.

The nitrogen source used in the inventive process is preferably ammonia, ammonium salts, or protein hydrolysates.

Further media additives which can be added are salts of the elements phosphorus, sulfur, chlorine, sodium, magnesium, nitrogen, potassium, calcium, iron and, in traces, (that is to say in μM concentrations), salts of the elements molybdenum, boron, cobalt, manganese, zinc and nickel.

In addition, organic acids (for example acetate, citrate), amino acids (for example isoleucine), and vitamins (e.g. B1, B6) can be added to the medium.

Complex nutrient sources which can be used are, for example, yeast extract, corn steep liquor, soybean flour or malt extract.

The pH of the fermentation medium is in the range of 4–10. Preference is given to a range of 6–8. Particular preference is given to a pH range from 6.5 to 7.5.

The incubation temperature is 15–45° C. Preference is given to a temperature of 30–37° C.

The fermentation is preferably carried out under aerobic growth conditions. The oxygen is introduced into the fermenter using compressed air or pure oxygen.

Microorganisms which are fermented according to the described process excrete, in a fermentation time of 1 to 4 days, the corresponding non-proteinogenic L-amino acids into the culture medium with high efficiency.

When a nucleophilic substance is fed, microorganisms having deregulated cysteine metabolism excrete, during the fermentation, non-proteinogenic amino acids of the general formula (6) in the L configuration:

$$\begin{array}{c} \text{COOH} \\ | \\ H_2N-C-H \\ | \\ CH_2 \\ | \\ Z \end{array} \quad (6)$$

where Z is a monovalent radical selected from the formulae (7) to (13)

$$-S-R^1, \quad (7)$$

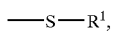
(8)

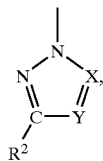
(9)

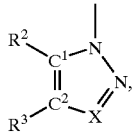
(10)

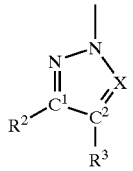
(11)

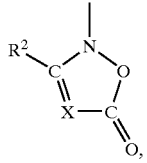
(12)

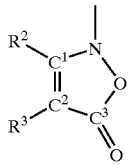
(13)

and their esters, ethers or salts, and $R^1$, $R^2$, $R^3$, $R^4$, X and Y have the meaning already specified under the formulae (1) to (5).

The inventive process makes it possible for the first time to produce compounds of the group 1,2,3,4-tetrazolyl-L-alanine and its derivatives, and 1,2,3-triazolyl-L-alanine and its derivatives. Preferably these are respectively the isomeric forms 1,2,3,4-tetrazol-1-yl-L-alanine (14) and 1,2,3,4-tetrazol-2-yl-L-alanine (15) and their derivatives including their esters, ethers or salts, and 1,2,3-triazol-1-yl-L-alanine (16) and 1,2,3-triazol-2-yl-L-alanine (17) and their derivatives, including their esters, ethers or salts,

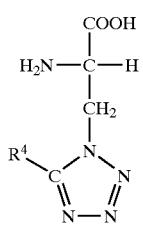
(14)

(15)

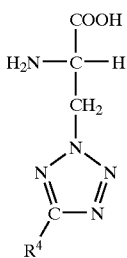

(16)

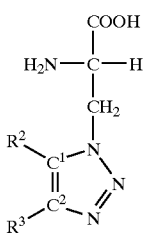

(17)

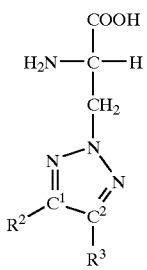

where $R^1$, $R^2$, $R^3$ and $R^4$ have the meaning specified above under the formulae (1) to (5).

The inventive process also makes it possible to produce for the first time compounds of the group S-heteroaryl-L-cysteines. These are in each case amino acid compounds having free amino and/or carboxylic acid functionalities. S-heteroaryl-L-cysteines are taken to mean cysteine derivatives which are characterized by substitution of a radical $R^7$ of the S atom. Here, $R^7$ is a heteroaryl radical that has aromatic character, is mono- or bicyclic, and, in addition to carbon atoms, has at least one heteroatom in a ring. Examples of heteroatoms are nitrogen, oxygen or sulfur. Heteroaryl radical can itself be substituted by a radical $R^4$, where $R^4$ has the meaning specified under formula (2).

(18)

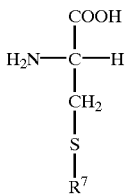

Examples of heteroaryl radicals are pyrrolyl, imidazolyl, pyrazolyl, triazolyl, tetrazolyl, thienyl, thiazolyl, oxazolyl, furanyl, pyridyl, pyrimidyl, pyrazinyl, benzimidazolyl, benzotriazolyl, benzoxazolyl, benzothiazolyl or purinyl.

The invention therefore relates to said compounds. Particularly preferred compounds are:

1,2,3,4-tetrazol-1-yl-L-alanine ($R^4$=H)
1,2,3,4-tetrazol-2-yl-L-alanine ($R^4$=H),
1,2,3-benzotriazol-1-yl-L-alanine ($R^2$ and $R^3$ are identical and are [—$CR^5$=$CR^6$—], where $R^5$ and $R^6$ are H and $R^2$ and $R^3$ are linked to form an aromatic ring),
1,2,3-benzotriazol-2-yl-L-alanine ($R^2$ and $R^3$ are identical and are [—$CR^5$=$CR^6$—], where $R^5$ and $R^6$ are H and $R^2$ and $R^3$ are linked to form an aromatic ring),
5-carboxy-1,2,3-benzotriazol-1-yl-L-alanine ($R^2$ and $R^3$ are different and are [—$CR^5$=$CR^6$—], where $R^5$ and $R^6$, in the case of $R^3$, are H and, in the case of $R^2$, $R^5$ is H and $R^6$ is——COOH, and $R^2$ and $R^3$ are linked to form an aromatic ring),
5-carboxy-1,2,3-benzotriazol-2-yl-L-alanine ($R^2$ and $R^3$ are different and are [—$CR^5$=$CR^6$—], where $R^5$ and $R^6$, in the case of $R^3$, are H and, in the case of $R^2$, $R^5$ is H and $R^6$ is —COOH, and $R^2$ and $R^3$ are linked to form an aromatic ring),
1,2,4-triazol-3-yl-L-cysteine,
thiazol-2-yl-L-cysteine,
imidazol-2-yl-L-cysteine,
thien-2-yl-L-cysteine,
pyridin-2-yl-L-cysteine,
pyrimidin-2-yl-L-cysteine,
benzothiazol-2-yl-L-cysteine,
benzoxazol-2-yl-L-cysteine.

Preferably, the product, after separating off the biomass, is isolated from the culture supernatant by known methods (for example filtration, centrifugation). Such methods for isolating amino acids are also known to those skilled in the art. They comprise, for example, extraction, adsorption, ion-exchange chromatography, precipitation, crystallization.

The examples below serve for further explanation of the invention. The bacteria strain *Escherichia coli* W3110/pA-CYC184-cysEX-GAPDH-ORF306, which was used for carrying out the examples, was deposited at the DSMZ (Deutsche Sammlung für Mikroorganismen und Zellkulturen GmbH, D-38142 Braunschweig) under the number DSM 13495 in accordance with the Budapest Treaty.

EXAMPLE 1

Preliminary Culture of the Production Strain

As a preliminary culture for the fermentation, 20 ml of LB medium (10 g/l of tryptone, 5 g/l of yeast extract, 10 g/l of NaCl) which additionally contain 15 mg/l of tetracycline were inoculated with strain W3110/pACYC184-cysEX-GAPDH-ORF306 (described in EP 0885962 A1, equivalent to the U.S. application having the Ser. No. 09/097759 (hereby incorporated by reference)) and incubated in a shaker at 30° C. and 150 rpm. After seven hours the entire batch was transferred into 100 ml of SM1 medium (12 g/l of $K_2HPO_4$; 3 g/l of $KH_2PO_4$; 5 g/l of $(NH_4)_2SO_4$; 0.3 g/l of $MgSO_4.7H_2O$; 0.015 g/l of $CaCl_2.2H_2O$; 0.002 g/l of $FeSO_4.7H_2O$; 1 g/l of $Na_3citrate.2H_2O$; 0.1 g/l of NaCl; 1 ml/l of trace element solution consisting of 0.15 g/l of $Na_2MoO_4.2H_2O$; 2.5 g/l of $Na_3BO_3$; 0.7 g/l of $CoCl_2.6H_2O$; 0.25 g/l of $CuSO_4.5H_2O$; 1.6 g/l of $MnCl_2.4H_2O$; 0.3 g/l of $ZnSO_4.7H_2O$), which was supplemented with 5 g/l of glucose; 0.5 mg/l of vitamin $B_1$ and 15 mg/l of tetracycline. Further incubation was performed at 30° C. for 17 hours at 150 rpm.

EXAMPLE 2

Production of S-[2,3-dihydroxy-4-mercaptobutyl]-L-cysteine by Fermentation

The fermenter used was a Biostat M instrument from Braun Biotech (Melsungen, Germany) having a maximum culture volume of 2 l. Using the preliminary culture described in Example 1 (optical density at 600 nm approximately 3), the fermenter was inoculated with 900 ml of fermentation medium (15 g/l of glucose; 10 g/l of tryptone; 5 g/l of yeast extract; 5 g/l of $(NH_4)_2SO_4$; 1.5 g/l of $KH_2PO_4$; 0.5 g/l of NaCl; 0.3 g/l of $MgSO_4.7H_2O$; 0.015 g/l of $CaCl_2.2H_2O$; 0.075 g/l of $FeSO_4.7H_2O$; 1 g/l of Na citrate.$2H_2O$ and 1 ml/l of trace element solution, see above, 5 mg/l of vitamin B1 and 15 mg/l of tetracycline, adjusted to pH 7.0 using 25% ammonia). During the fermentation, a temperature of 32° C. was set and the pH was kept constant at a value of 7.0 by adding 25% ammonia. The culture was treated with sterilized compressed air at 1.5 vol/vol/min and stirred at an agitator speed of 200 rpm. After the oxygen saturation had decreased to a value of 50%, the speed was increased via a control apparatus up to a value of 1 200 rpm, in order to maintain 50% oxygen saturation (determined using a pO2 probe, calibrated to 100% saturation at 900 rpm).

After eight hours, a 1 M dithiothreitol solution was added at a rate of 2 mmol/h. Glucose was applied from a 56% stock solution as soon as the content in the fermenter had decreased from initially 15 g/l to approximately 5–10 g/l. The glucose was fed at a flow rate of 8–14 ml/h, which kept the glucose concentration constant between 0.5 and 10 g/l. The glucose was determined using a glucose analyzer from YSI (Yellow Springs, Ohio, USA).

The fermentation time was 48 hours. After this time samples were taken and the cells were removed from the culture medium by centrifugation. The resultant culture supernatants were fractionated by reversed-phase HPLC on a LUNA 5 μ C18(2) column (Phenomenex, Aschaffenburg, Germany). The eluent used was dilute phosphoric acid (0.1 ml of concentrated phosphoric acid/l) at a flow rate of 0.5 ml/min. S-mercaptodihydroxybutyl-L-cysteine was eluted at a retention time of 86.7 min. The yield was 2.5 g/l.

EXAMPLE 3

Production of S-phenyl-L-cysteine by Fermentation

The bacteria were cultured as described in Examples 1 and 2. After eight hours, a 1 M Na thiophenol suspension was added at a rate of 2 mmol/h. S-phenyl-L-cysteine is eluted at a retention time of 88 min using the HPLC method described in Example 2. The yield was 2.1 g/l.

EXAMPLE 4

Production of 1,2-pyrazolyl-L-alanine by Fermentation

The bacteria were cultured as described in Examples 1 and 2. After eight hours, a 1 M 1,2-pyrazole solution was added at a rate of 4 mmol/h. 1,2-pyrazolyl-L-alanine is eluted at a retention time of 8.4 min using the HPLC method described in Example 2. The yield was 6.1 g/l.

EXAMPLE 5

Production of 1,2,4-triazolyl-L-alanine by Fermentation

The bacteria were cultured as described in Examples 1 and 2. After eight hours, a 1 M 1,2,4-triazole solution was added at a rate of 4 mmol/h. 1,2,4-triazol-1-yl-L-alanine is eluted at a retention time of 5.8 min using the HPLC method described in Example 2. The yield was 4.6 g/l.

EXAMPLE 6

Production of 1,2,3,4-tetrazolyl-L-alanine by Fermentation

The bacteria were cultured as described in Examples 1 and 2. After eight hours, a 1 M 1,2,3,4-tetrazole solution was added at a rate of 4 mmol/h. During the fermentation the two isomers 1,2,3,4-tetrazol-1-yl-L-alanine and 1,2,3,4-tetrazol-2-yl-L-alanine are formed. These are eluted at a retention time of 5.4 and 5.7 min, respectively, using the HPLC method described in Example 2. The yield, as a total of the two isomers, was 3.9 g/l.

EXAMPLE 7

Production of 5-carboxy-1,2,3-benzotriazolyl-L-alanine by Fermentation

The bacteria were cultured as described in Examples 1 and 2. After eight hours, a suspension of 1 M 1,2,3-benzotriazol-5-carboxylic acid in 0.5 M NaOH was added at a rate of 4 mmol/h. During the fermentation all three isomers 5-carboxy-1,2,3-benzotriazol-1-yl-L-alanine, 5-carboxy-1,2,3-benzotriazol-2-yl-L-alanine and 5-carboxy-1,2,3-benzotriazol-3-yl-L-alanine are formed, but the main product is 5-carboxy-1,2,3-benzotriazol-2-yl-L-alanine. This is eluted at a retention time of 67.5 min using the HPLC method described in Example 2. The yield was 5.2 g/l.

EXAMPLE 8

Production of 1,2,4-oxadiazolidine-2,5-dionyl-L-alanine (=quisqualic acid) by Fermentation The bacteria were cultured as described in Examples 1 and 2. After eight hours, a 2 M solution of 1,2,4-oxadiazolidine-2,5-dione in dimethyl sulfoxide was added at a rate of 2 mmol/h. Quisqualic acid is eluted at a retention time of 5.6 min using the HPLC method described in Example 2. The yield was 2.2 g/l.

EXAMPLE 9

Isolation of 1,2-pyrazolyl-L-alanine from Fermenter Broth

The cells were first removed by centrifugation of 0.6 l of fermenter broth at 5 000 g. 10 g of activated carbon were added to the supernatant for decolorization, the mixture was stirred for 2 h at room temperature and then filtered. The resultant solution was adjusted to a pH of 6.0 using 2 M NaOH, applied to a cation-exchange column Amberjet 1200/H+ (Rohm and Haas S. A., Chauny, France; 250 ml gel bed) and bound substances were eluted with 1 M NaCl. The elution fractions were combined (500 ml), adjusted to a pH of 6.0 with 2 M NaOH and concentrated to 100 ml. The sample was stored for 16 h at 4° C. The resulting crystals were recovered by filtration, washed with 50 ml of ethanol and then dried.

EXAMPLE 10

Production of S-thiazol-2-yl-L-cysteine by Fermentation

The bacteria were cultured as described in Examples 1 and 2. After eight hours, a 1 M 2-mercaptothiazole solution was added at a rate of 2 mmol/h. S-Thiazol-2-yl-L-cysteine is eluted at a retention time of 33.7 min using the HPLC method described in Example 2. The yield was 6.1 g/l.

EXAMPLE 11

Production of S-1,2,4-triazol-3-yl-L-cysteine by Fermentation

The bacteria were cultured as described in Examples 1 and 2. After eight hours, a 1 M 3-mercaptotriazole solution was added at a rate of 2 mmol/h. S-Thiazol-2-yl-L-cysteine is eluted at a retention time of 8.2 min using the HPLC method described in Example 2. The yield was 5.5 g/l.

Accordingly, while a few embodiments of the present invention have been shown and described, it is to be understood that many changes and modifications may be made thereunto without departing from the spirit and scope of the invention as defined in the appended claims.

What is claimed is:

1. A process for producing non-proteinogenic L-amino acids by direct fermentation of a microorganism strain having a deregulated cysteine metabolism in a manner which comprises, during the fermentation, adding a nucleophilic compound to a fermentation batch in amounts such that this leads to the production of non-proteinogenic L-amino acids by the microorganism strain;

wherein the nucleophilic compound is added selected from the following group consisting of:

thiol of the general formula (1):

(1)

where $R^1$ is monovalent substituted or unsubstituted alkyl, alkoxy, aryl or heteroaryl radical having a maximum of 15 carbon atoms;

azole of the general formula (2) or (3):

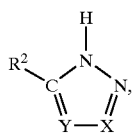

(2)

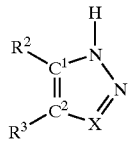

(3)

and their esters, ethers or salts, where X and Y are identical or different and X and Y denote $CR^4$ or N, with proviso that at least one of X or Y is N, and $R^4$ is —H, —COOH, —OH, —NH$_2$, —NO$_2$, —SH, —SO$_3$, —F, —Cl, —Br, —I, $C_1$–$C_5$-alkylcarbonyl- or $R^1$, and $R^1$ has the meaning where $R^1$ is monovalent substituted or unsubstituted alkyl, alkoxy, aryl or heteroaryl radical having a maximum of 15 carbon atoms;

where $R^2$ and $R^3$ are identical or different and are $R^4$ and $R^4$ is —H, —COOH, —OH, —NH$_2$, —NO$_2$, —SH, —SO$_3$, —F, —Cl, —Br, —I, $C_1$–$C_5$-alkylcarbonyl- or $R_1$, and $R^1$ has the meaning specified above;

or where $C^1$ and $C^2$ in formula (3), instead of the substituents $R^2$ and $R^3$ are linked by means of a bridge [—CR$^5$R$^6$—]$_a$, where a is 1, 2, 3 or 4, to form a ring, where $R^5$ and $R^6$ are identical or different and are $R^4$ and $R^4$ is —H, —COOH, —OH, —NH$_2$, —NO$_2$, —SH, —SO$_3$, —F, —Cl, —Br, —I, $C_1$–$C_5$-alkylcarbonyl or $R^1$, and $R^1$ has the meaning where $R^1$ is monovalent substituted or unsubstituted alkyl, alkoxy, aryl or heteroaryl radical having a maximum of 15 carbon atoms;

one or more non-adjacent groups [—CR$^5$R$^6$—] can be replaced by oxygen, sulfur, or an imino radical, which may be unsubstituted or substituted by $C_1$–$C_5$-alkyl, and two adjacent groups [—CR$^5$R$^6$—] can be replaced by a group [—CR$^5$=CR$^6$—] or by a group [—CR$^5$=N—];

isoxazolinone of the general formula (4) or (5):

(4)

(5)

and their esters, ethers or salts, where X, $R^1$, $R^2$, $R^3$ have the meaning where X is $CR^4$ or N, and $R^4$ is —H, —COOH, —OH, —NH$_2$, —NO$_2$, —SH, —SO$_3^-$, —F, —Cl, —Br, —I, $C_1$–$C_5$-alkylcarbonyl- or $R^1$, and $R^1$ has the meaning where $R^1$ is monovalent substituted or unsubstituted alkyl, alkoxy, aryl or heteroaryl radical having a maximum of 15 carbon atoms; and where $R^2$ and $R^3$ are identical or different and are $R^4$, where $C^1$ and $C^2$ in formula (5), instead of the substituents $R^2$ and $R^3$, can be linked by means of a bridge defined as for formula (3) to form a ring.

2. The process as claimed in claim 1, wherein the non-proteinogenic L-amino acid is an amino acid of the general formula (6) in the L configuration:

(6)

where Z is a monovalent radical selected from the formulae (7) to (13):

(7)

(8)

(9)

-continued

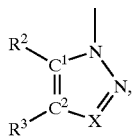
(10)

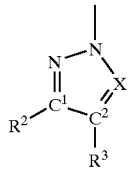
(11)

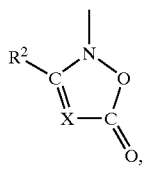
(12)

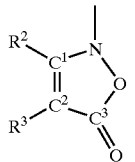
(13)

and their esters, ethers or salts, and $R^1$, $R^2$, $R^3$, $R^4$, X and Y have the meaning as follows:

where $R^1$ is monovalent substituted or unsubstituted alkyl, alkoxy, aryl or heteroaryl radical having a maximum of 15 carbon atoms;

for formulae (8) and (9), where X and Y are identical or different and X and Y denote $CR^4$, or N, with the proviso that at least one of X or Y is N, and $R^4$ is —H, —COOH, —OH, —NH$_2$, —NO$_2^-$, —SH, —SO$_3^-$, —F, —Cl, —Br, —I, $C_1$–$C_5$-alkylcarbonyl- or $R^1$, and $R^1$ has the meaning specified above, where $R^2$ and $R^3$ are identical or different and are $R^4$;

for formulae (10) and (11),

X is N, and $R^2$ and $R^2$ are as defined above;

for formulae (12), where X denotes $CR^4$ or N $R^4$ is —H, —COOH, —OH, —NH$_2$, —NO$_2^-$, —SH, —SO$_3^-$, —F, —Cl, —Br, —I, $C_1$–$C_5$-alkylcarbonyl- or $R^1$, and $R^1$ has the meaning specified above, and where $R^2$ is $R^4$.

3. A process for producing non-proteinogenic L-amino acids by direct fermentation of a microorganism strain having a deregulated cysteine metabolism in a manner which comprises, during the fermentation, adding a nucleophilic compound to a fermentation batch in amounts such that this leads to the production of non-proteinogenic L-amino acids by the microorganism strain;

wherein the nucleophilic compound is added selected from the following group consisting of:

thiol of the general formula (1):

(1)

where $R^1$ is monovalent substituted or unsubstituted alkyl, alkoxy, aryl or heteroaryl radical having a maximum of 15 carbon atoms;

azole of the general formula (2) or (3):

(2)

(3)

and their esters, ethers or salts, where X and Y are identical or different and X and Y denote $CR^4$ or N, and $R^4$ is —COOH, —OH, —NH$_2$, —NO$_2^-$, —SH, —SO$_3^-$, —F, —Cl, —Br, —I, $C_1$–$C_5$-alkylcarbonyl- or $R^1$, and $R^1$ has the meaning where $R^1$ is monovalent substituted or unsubstituted alkyl, alkoxy, aryl or heteroaryl radical having a maximum of 15 carbon atoms;

where $R^2$ and $R^3$ are identical or different and are $R^4$ or where $C^1$ and $C^2$ in formula (3), instead of the substituents $R^2$ and $R^3$, are linked by means of a bridge $[—CR^5R^6—]_a$, where a is 1, 2, 3 or 4, to form a ring, where $R^5$ and $R^6$ are identical or different and are $R^4$ and $R^4$ is —COOH, —OH, —NH$_2$, —NO$_2^-$, —SH, —SO$_3^-$, —F, —Cl, —Br, —I, $C_1$–$C_5$-alkylcarbonyl- or $R^1$, and $R^1$ has the meaning where $R^1$ is monovalent substituted or unsubstituted alkyl, alkoxy, aryl or heteroaryl radical having a maximum of 15 carbon atoms;

one or more non-adjacent groups $[—CR^5R^6—]$ can be replaced by oxygen, sulfur, or an imino radical, which may be unsubstituted or substituted by $C_1$–$C_5$-alkyl, and two adjacent groups $[—CR^5R^6—]$ can be replaced by a group $[—CR^5=CR^6—]$ or by a group $[—CR^5=N—]$;

isoxazolinone of the general formula (4) or (5):

(4)

(5)

and their esters, ethers or salts, where X, $R^1$, $R^2$, $R^3$ have the meaning where X denotes $CR^4$ or N, and $R^4$ is —COOH, —OH, —NH$_2$, —NO$_2^-$, —SH, —SO$_3^-$, —F, —Cl, —Br, —I, $C_1$–$C_5$-alkylcarbonyl- or $R^1$, and $R^1$ has the meaning where $R^1$ is monovalent substituted or unsubstituted alkyl, alkoxy, aryl or heteroaryl radical having a maximum of 15 carbon atoms;

where $R^2$ and $R^3$ are identical or different and are $R^4$ and where $C^1$ and $C^2$ in formula (5), instead of the substituents $R^2$ and $R^3$, can be linked by means of a bridge defined as for formula (3) to form a ring.

* * * * *